(12) United States Patent
Anderson et al.

(10) Patent No.: US 11,666,910 B2
(45) Date of Patent: Jun. 6, 2023

(54) MICROFLUIDIC DEVICES

(71) Applicant: HEWLETT-PACKARD DEVELOPMENT COMPANY, L.P., Spring, TX (US)

(72) Inventors: Daryl E. Anderson, Corvallis, OR (US); George H. Corrigan, III, Corvallis, OR (US); Alexander Govyadinov, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 17/268,394

(22) PCT Filed: Nov. 26, 2018

(86) PCT No.: PCT/US2018/062480
§ 371 (c)(1),
(2) Date: Feb. 12, 2021

(87) PCT Pub. No.: WO2020/112081
PCT Pub. Date: Jun. 4, 2020

(65) Prior Publication Data
US 2021/0178385 A1 Jun. 17, 2021

(51) Int. Cl.
*B01L 7/00* (2006.01)
*C12Q 1/686* (2018.01)
*B01L 3/00* (2006.01)

(52) U.S. Cl.
CPC .......... *B01L 3/50273* (2013.01); *B01L 7/525* (2013.01); *C12Q 1/686* (2013.01);
(Continued)

(58) Field of Classification Search
CPC ........ B01L 3/50273; B01L 2200/0673; B01L 7/525; C12M 41/40; C12M 1/38;
(Continued)

(56) References Cited

U.S. PATENT DOCUMENTS

| 7,338,637 B2 | 3/2008 | Pease |
| 9,387,478 B2 | 7/2016 | Bergstedt |

(Continued)

FOREIGN PATENT DOCUMENTS

| DE | 102004050139 A1 | 4/2006 |
| WO | WO-03012406 A1 | 2/2003 |
| WO | WO-20181 00421 | 6/2018 |

OTHER PUBLICATIONS

Chiou et al., "A Closed-Cycle Capillary Polymerase Chain Reaction Machine," Analytical Chemistry, vol. 73, pp. 2018-2021. (Year: 2001).*

(Continued)

*Primary Examiner* — Young J Kim
(74) *Attorney, Agent, or Firm* — Foley & Lardner LLP (57) ABSTRACT

In one example in accordance with the present disclosure, a microfluidic device is described. The microfluidic device includes a reservoir to contain a first thermally expandable fluid, a first heater to heat the thermally expandable fluid in the reservoir, a channel extending from the reservoir and connected to the reservoir at a first opening, and a liquid volume obstructing the channel.

17 Claims, 7 Drawing Sheets

(52) U.S. Cl.
CPC ............... *B01L 2200/0673* (2013.01); *B01L 2300/0645* (2013.01); *B01L 2300/1827* (2013.01); *B01L 2400/0442* (2013.01)

(58) Field of Classification Search
CPC .. C12M 23/16; C12Q 1/686; C12Q 2565/607; C12Q 2565/629
See application file for complete search history.

(56) References Cited

U.S. PATENT DOCUMENTS

| | | |
|---|---|---|
| 9,909,171 B2 | 3/2018 | Joseph |
| 2003/0175947 A1* | 9/2003 | Liu ..................... B01F 33/30 422/68.1 |
| 2016/0310949 A1 | 10/2016 | Kwang |

OTHER PUBLICATIONS

Chang, "Integrated polymerase chain reaction chips utilizing digital microfluidics", May 20, 2006, SpringerLink.

Gransee, "Fluorescence detection in Lab-on-a-chip systems using ultrafast nucleic acid amplification methods", May 22, 2014, SPIE, Germany.

Zhang, "Miniaturized PCR chips for nucleic acid amplification and analysis: latest advances and future trends", Nucleic Acids Research, Jun. 18, 2007, vol. 35, No. 13, China.

\* cited by examiner

MICROFLUIDIC DEVICES

BACKGROUND

Microfluidic devices are used in a variety of disciplines including engineering, physics, chemistry, microtechnology, and biotechnology. Microfluidics involves the study of small volumes, e.g., microliters, picoliters, and/or nanoliters, of fluid and how to manipulate, control and use such small volumes of fluid in various microfluidic systems and devices such as microfluidic devices or chips. For example, microfluidic biochips (which may also be referred to as "lab-on-chip") are used in the field of molecular biology to integrate assay operations for purposes such as analyzing enzymes and DNA, detecting biochemical toxins and pathogens, diagnosing diseases, etc. One operation which could be performed using a microfluidic biochip is Polymerase Chain Reaction (PCR).

Polymerase Chain Reaction is a method for amplifying nucleic material. PCR involves mixing a target DNA sequence to be amplified with primers and nucleotides. The two strands of the double helix of the sample are separated using heat. This is referred to as "melting" or "denaturing." Next, the temperature is lowered and primers are bound to the complementary sequences of DNA. This is called "annealing" or "priming." The two DNA strands then become templates for DNA polymerase to enzymatically assemble new DNA strands from the nucleotides. This is called "extension." The cycle is repeated, with the number of copies of the target DNA sequence doubling each time. PCR includes a large number of variant procedures and additional operations which may be useful to achieve specific outcomes, but they build on this basic three operation cycle.

BRIEF DESCRIPTION OF THE DRAWINGS

The accompanying drawings illustrate various examples of the principles described herein and are a part of the specification. The illustrated examples do not limit the scope of the claims.

Throughout the drawings, identical reference numbers designate similar, but not necessarily identical, elements. The figures are not necessarily to scale, and the size of some parts may be exaggerated or minimized to more clearly illustrate the example shown. The drawings provide examples and/or implementations consistent with the description. However, the description is not limited to the examples and/or implementations shown in the drawings.

DETAILED DESCRIPTION

For simplicity and illustrative purposes, the present specification is described by referring mainly to an example thereof. In the following description, numerous specific details are set forth in order to provide a thorough understanding of the present specification. It will be readily apparent, however, that the present specification may be practiced without limitation to these specific details. In other instances, some methods and structures have not been described in detail so as not to unnecessarily obscure the present specification. As used herein, the terms "a" and "an" are intended to denote at least one of a particular element, the term "includes" means includes but not limited to, the term "including" means including but not limited to, and the term "based on" means based at least in part on.

Additionally, it should be understood that the elements depicted in the accompanying figures may include additional components and that some of the components described in those figures may be removed and/or modified without departing from scopes of the elements disclosed herein. It should also be understood that the elements depicted in the figures may not be drawn to scale and thus, the elements may have different sizes and/or configurations other than as shown in the figures.

As used in this specification and the associated claims, the term "fluid" should be understood as encompassing liquids and gases as well as compositions which flow under pressure, e.g., slurries, colloids, etc. The term "liquid" includes liquid compositions which include solids and/or gasses (e.g. as particles and/or bubbles).

Unless otherwise stated, all values include an implicit tolerance of 20% from the recited value. So, a range of 100 to 200° C. would cover 80 to 240° C. because 20% of 100 is 20. Accordingly the value 100° C. encompasses 80 to 120° C. Also, as 20% of 200 is 40, 200° C. encompasses 160 to 240° C. When provided, tolerances will include an appropriate +/− indicator (or +first value/−second value) to provide specificity.

Among other examples, this specification describes a microfluidic device. The microfluidic device includes a reservoir to contain a thermally expandable fluid; a heater to heat the thermally expandable fluid in the reservoir; a channel extending from the reservoir, the channel connected to the reservoir at a first opening; and a liquid volume obstructing the channel.

This specification also describes a method of performing polymerase chain reaction (PCR). According to the method, a liquid volume, including a primer, an amplification target, and bases, is provided to a channel of a microfluidic device. The microfluidic device includes a first reservoir to contain a first thermally expandable fluid; a first heater to heat the first thermally expandable fluid in the first reservoir; a second reservoir to contain a second thermally expandable fluid; a second heater to heat the second thermally expandable fluid in the second reservoir; the channel connecting the first reservoir and the second reservoir; a first heating zone in the channel; and a second heating zone in the channel. The first heater and second heater are heated to move the liquid volume back and forth between the first and second heating zones of the channel by expansion of the thermally expandable fluids in the first reservoir and second reservoir.

This specification describes a method of using a microfluidic device. According to the method, a liquid volume is provided to the microfluidic device. The microfluidic device includes a reservoir to contain a thermally expandable fluid, a heater to heat the thermally expandable fluid in the reservoir, and a channel connected to the reservoir and extending from the reservoir. The thermally expandable fluid in the reservoir is heated to adjust a location of the liquid volume in the channel. The heated thermally expandable fluid expands and pushes the liquid volume in the channel.

Polymerase Chain Reaction (PCR) is a method to amplify nucleic material. PCR includes a series of operations which are repeated in a cycle. With each cycle, the number of copies of the nucleic material double. Accordingly, PCR provides a method to amplify a single strand of nucleic material into a sample large enough for a variety of testing methods.

The basic operations of PCR are 1) melting (also called denaturation), 2) priming (also called annealing), and 3) extension (also called elongation). In the first operation, the temperature of the solution containing the nucleic acid sequence is raised to cause the paired strands of the replication target to separate. In the second operation, primers are attached to the ends of each of the strands. This is performed at a cooler temperature than the first operation, with the specific temperature dependent on the primers, the primer concentration, and other factors. In the third operation, the polymerase builds the complementary strands starting at the primers, producing a pair of bound strands of the nucleic material. The temperature for extension may be the same as that for priming. In some cases, the extension speed may be optimized by use of a third temperature.

A wide variety of variations and additional operations may be used with PCR. For example, preheating and/or post holding at temperature are used with PCR. As another example, the amplified material may be subject to secondary processes and/or testing. For example, the amplified material may be sequenced. As yet another example, the amplified material may be cut with a restriction enzyme (or multiple restriction enzymes) and the fragmentation pattern analyzed and/or sequenced. Probes and/or other fragment binding may be used to assess the sequence and/or identify the presence and/or absence of a specific allele(s).

Figure 1:
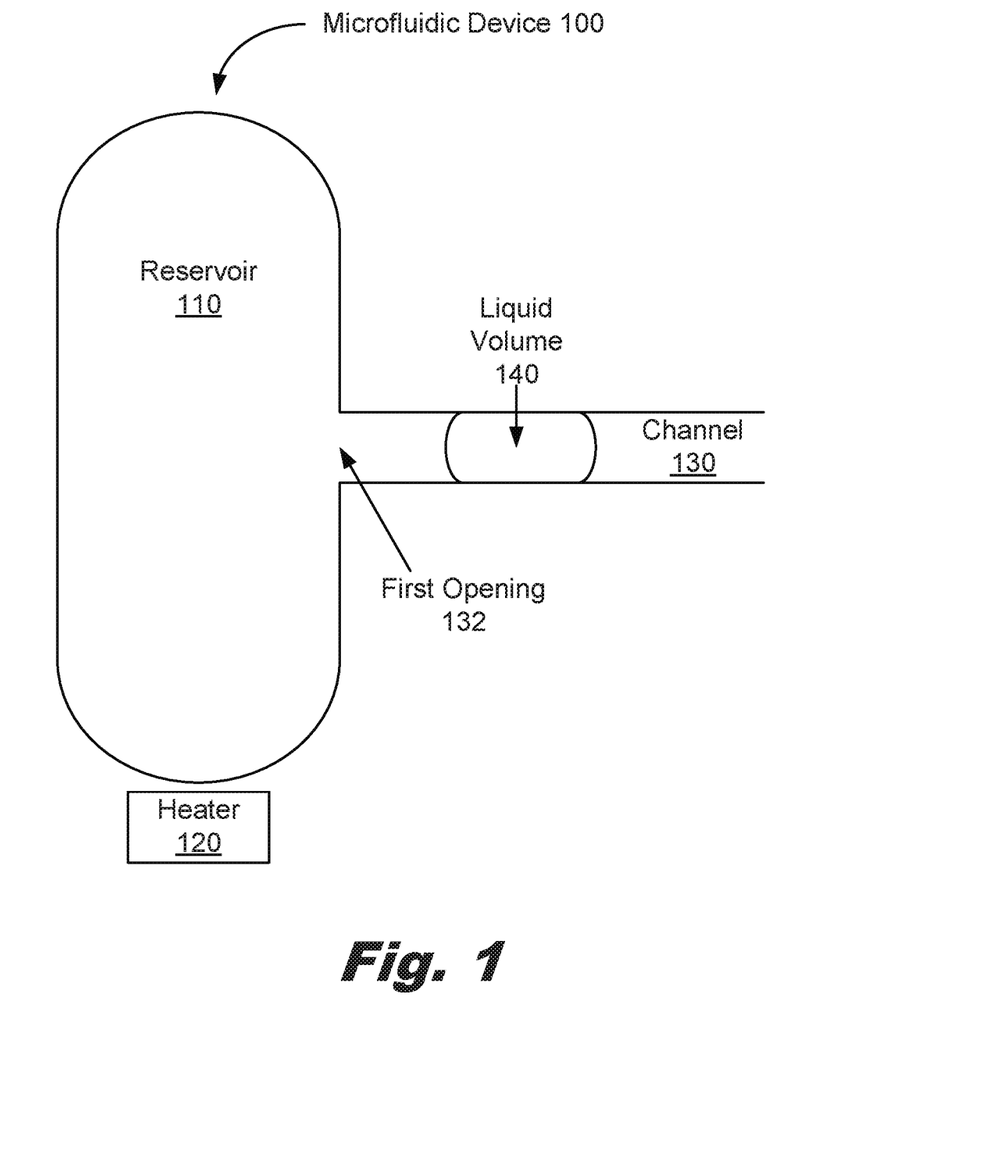
FIG. 1 shows an example of a microfluidic device consistent with this specification.

Turning now to the figures, FIG. 1 shows a microfluidic device (100) consistent with this specification. In this example, the microfluidic device (100) includes a reservoir (110) to contain a thermally expandable fluid; a heater (120) to heat the thermally expandable fluid in the reservoir; a channel (130) extending from the reservoir (110), the channel (130) connected to the reservoir (110) at a first opening (132); and a liquid volume (140) obstructing the channel (130).

The described microfluidic device (100) allows control over motion of a liquid volume (140) in a channel (130). A reservoir (110) contains a thermally expandable fluid. This fluid is heated and expands. When the fluid expands, the fluid increases the pressure in the channel (130) extending from the reservoir (110). The channel (130) is obstructed by the liquid volume (140). However, the expanding fluid pushes the liquid volume (140) in the channel (130).

As described above, the reservoir (110) holds a thermally-expandable fluid. In some examples, the fluid may be a gas. For example, the fluid may be air. As another example, the fluid may be an inert gas such as argon. In other examples, the thermally expandable fluid may be a liquid. Liquids have greater thermal conductivity but lower coefficients of thermal expansion than gases. In the present system, it may be desirable to have a high thermal conductivity but also to have a large coefficient of thermal expansion. Accordingly, the selected thermally-expandable fluid may depend on other factors of the microfluidic device (100).

The reservoir (110) may hold other materials as well. However, decreasing the volume in the reservoir (110) increases the temperature change to get the same expansion and move the liquid volume (140). Further, if the volume of the reservoir (110) changes, control of the liquid volume (140) may be more difficult.

The reservoir (110) may be sealable with the exception of the channel (130). In some examples, the reservoir (110) contains no other openings beyond the first opening (132) connecting the reservoir (110) to the channel (130). In other examples, the reservoir (110) contains other openings. These other openings may be sealable to prevent the thermally-expandable fluid from exiting through them.

In one example, the reservoir (110) may have a plurality of channels (130) extending in parallel from the reservoir (110). These channels (130) may each contain a liquid volume (140) and pressure changes from the reservoir (110) may move all the liquid volumes (140) together.

The thermally expandable fluid should not disrupt the droplet of the liquid volume (140) and/or intermix with the liquid volume (140). While all gases have some solubility in almost all liquids, it is desirable for the surface tension of the liquid volume (140) to keep the liquid volume (140) intact and for the liquid volume (140) to move as a unit in the channel (130).

The heater (120) heats the thermally-expandable fluid in the reservoir (110). In one example, the heater (120) may be integrated into a surface of the reservoir (110). In another example, the heater (120) may heat the thermally-expandable fluid in the reservoir (110) through a wall of the reservoir (110). In an example, the heater (120) is a resistive heater (120), a bank of resistive heaters (120), and/or a series of resistive heaters (120). In an example, a group of resistive heaters (120) is organized to induce flow of the thermally expandable fluid in the reservoir (110) to enhance mixing and temperature uniformity. For example, the heater (120) may be located at a bottom surface of the reservoir (110) along a first wall of the reservoir (110). In some examples, the reservoir (110) may include a temperature sensor to facilitate control over the heating of the reservoir (110). In some examples, the reservoir (110) contains filaments (e.g., a mesh) and/or similar non-uniformities to induce turbulence and mixing in the reservoir (110).

The channel (130) connects to the reservoir (110) at the first opening (132), allowing the thermally-expandable fluid in the reservoir (110) to expand into the channel (130) and push the liquid volume (140). The channel (130) may include a variety of zones and/or sensors. The device (100) may move the liquid volume (140) back and forth in the channel (130) between the different zones and/or sensors. The different zones may have different temperatures. That is, the channel (130) may include multiple heating zones at multiple temperatures. For example, the channel (130) may include a first heating zone at a first temperature and a second heating zone at a second temperature. The heating zones may be continuous and/or adjacent to each other. That is, the heating zones maybe separated by unheated portions of the channel (130).

In some examples, the channel (130) may include a surface modification to reduce wetting of the surface of the channel (130) by the liquid volume (140). For example, for an aqueous liquid volume (140), the channel (130) may include a hydrophobic surface layer to reduce spread of the liquid volume (140) on the channel (130) walls. This may also reduce the force to be applied to move the liquid volume (140) in the channel (130).

In an example, the microfluidic device (100) is used to perform polymerase chain reaction (PCR). In this example, the liquid volume (140) may contain an amplification target, primers, bases, and a polymerase enzyme. The liquid volume (140) may be formed using a master mix. The liquid volume (140) may be pushed back and forth between multiple heated zones to produce a desired time-temperature profile to perform the thermal cycles of PCR.

Within the system, a first opening (132) connects the channel (130) to the reservoir (110). In some examples, the first opening (132) may have cross-sectional dimensions similar to the remainder of the channel (130) while in others, the first opening (132) may have a smaller or larger cross section than the remainder of the channel (130). The first opening (132) allows movement of the thermally-expandable fluid into the channel (130) to push the liquid volume (140) along the channel (130). The liquid volume (140) obstructing the channel (130) is moveable under the control of the heater (120). For example, the heater (120) expands the thermally expandable fluid, which pushes the liquid volume (140) along the channel (130).

Figure 2:
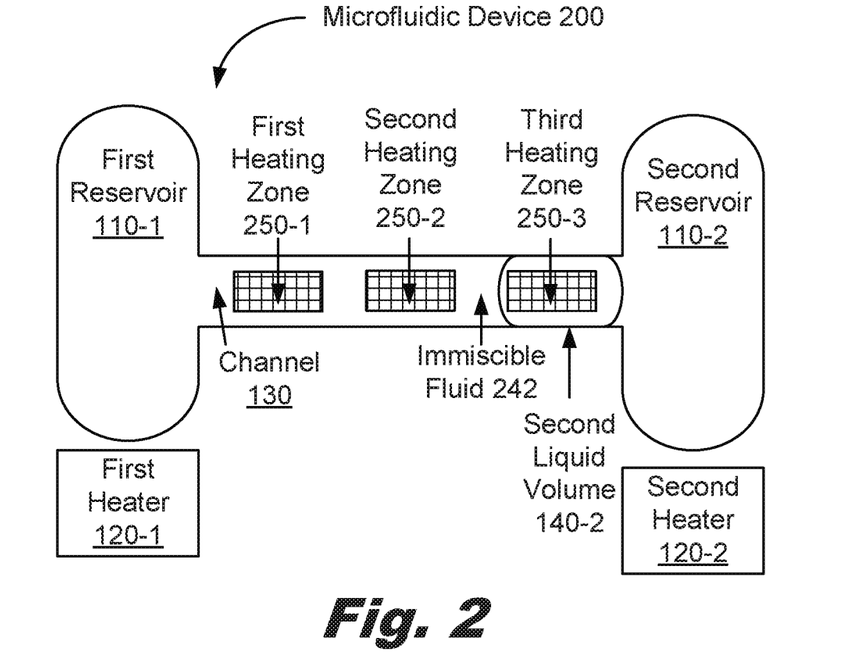
FIG. 2 shows an example of a microfluidic device consistent with this specification.

Turning to FIG. 2, In one example, the microfluidic device (100) further includes a second reservoir (110-2) containing a thermally expandable fluid. The second reservoir (110-2) is connected to a second end of the channel (130). The second reservoir (110-2) having an associated second heater (120-2), such that alternating heating of the first reservoir (110-1) and second reservoir (110-2) moves the liquid volume (140) between the first heating zone and the second heating zone based on expansion of the fluid in the reservoirs (110). Having reservoirs (110) attached to separate (e.g., both) ends of the channel (130) allows the liquid volume (140) to be pushed from either side. In contrast, depending on cooling of the thermally-expandable fluid in the first reservoir (110) to pull the liquid volume back may be less reliable and/or take more time.

As described above, the channel (130) may include a first heating zone (250-1) at a first temperature and a second heating zone (250-2) at a second temperature. The channel (130) may include additional heating zones. The additional heating zones allow additional liquid volumes (140) to be moved back and forth together. For example, the channel (130) may include a third heating zone (250-3) and the microfluidic device (200) may include a second liquid volume (140-2) in the channel (130) separated from the first liquid volume (140-1). An immiscible fluid (242) may separate the first liquid volume (140-1) and the second liquid volume (140-2). For example, if the first and second liquid volumes (140) are water based, the inclusion of an oil between them may help keep the first and second liquid volumes (140) separate as well as allow the pressure from the thermally-expandable fluid on the first liquid volume (140-1) to be transferred to the second liquid volume (140-2). Similarly, if the first and second liquid volumes (140) are an oil phase, for example, with digital PCR samples, then an aqueous separator between the first and second liquid volumes (140) may accomplish the goals of keeping the liquid volumes (140) separate and helping transfer the force from the expanding thermally-expandable fluid.

A long chain of test samples separated by non-miscible spacing fluid may be provided to the microfluidic device (100) and then cycled over a series of thermal zones. In some examples, the microfluidic device (100) is operated in a continuous or semi-continuous manner so that the liquid volumes (140) move through the thermal zones but do not have a period where the liquid volume (140) is static in a thermal zone. Further examples along this line are described in more detail below under FIGS. 5 and 6.

Returning to FIG. 1, the channel (130) may include a port to provide the liquid volume (140) into the channel (130). The port may also introduce the separating non-miscible fluid into the channel (130). In an example, the port includes a luer and/or similar fitting, for example, with a three-way port, allowing the port to be open and closed as needed to load samples. The port may include a membrane to allow a needle to pass through and inject material into the channel (130). In some examples, the port may also serve to remove the processed sample(s).

In some examples, the channel (130) may include a sensor. The sensor may be placed between a pair of heating zones and in some examples, the channel (130) includes multiple sensors, each sensor disposed between each pair of heating zones. The sensors detect fluid in a heating zone.

The sensor may be an optical sensor. The optical sensor may be used to monitor reactions, and/or assess outcomes. In an example, the optical sensor is used to estimate a concentration of DNA in a liquid volume. The optical sensor may detect the binding of a probe. The optical sensor may detect an indicator. In some examples, the optical sensor may operate in the visible spectrum. In other examples, the optical sensor may include wavelengths outside the visible spectrum including ultraviolet and/or infrared. In one example of operation, the optical sensor acquires a spectrum or spectra of the liquid volume (140). That spectrum may be processed to extract bond, composition, atomic composition, and/or other information. In another example, the optical sensor is used to detect the passage of the liquid volume (140) through a detection region of the channel (130).

The sensor may measure DNA concentration using another method, for example, via electrical measurements of capacitance of the liquid volume (140). In an example, the sensor uses potentiometric (pH) and/or electrochemical measurement to assess DNA concentration. The sensor may include a functionalized electrode or multiple functionalized electrodes. In an example, the sensor measures a nucleotide concentration and determines an amount of formed DNA based on the measurement. In an example, a time series of measurements from an electrode are compared to monitor a PCR process.

The sensor may be a conductivity, impedance, and/or other electrical property sensor. Such a sensor may have a pair of metal electrodes which detect when a conductive liquid bridges the area between them. In an example, the sensor detects an electrical property of a liquid volume (140) between them. The sensor may also measure and/or detect the presence of an immiscible fluid between the two electrodes.

In an example, the resistance of a heater (120) may be used to estimate the temperature of the liquid volume (140) in the heating zone. In one example, a heater (120) may contact the liquid volume (140) indirectly, for example, through a resistive layer and/or through a wall. In another example, an electrode makes direct contact with the liquid volume (140). The heater (120) may include an oxide layer, a tantalum layer, and/or other protective coating to electrically insulate the heater (120), and/or reduce damage from the high temperatures and/or vapor bubble formation. In contrast, electrodes for sensors tend to provide little to effectively no current and generate minimal heat as a result. The heater (120) may have an associated temperature sensor.

The temperature sensor may be used to control the signal provided to the heater (120). The temperature sensor may detect the temperature in a heating zone of the channel (130) heated by a heater (120).

FIG. 2 shows an example of a microfluidic device (200) consistent with this specification. In this example, the microfluidic device (200) includes a first reservoir (110-1) to contain a thermally-expandable fluid and a first heater (120-1) to heat the thermally-expandable fluid of the first reservoir (110-1). The microfluidic device (200) also includes a second reservoir (110-2) to contain a thermally-expandable fluid; a second heater (120-2) to heat the thermally-expandable fluid of the second reservoir (110-2). A channel (130) connects the first reservoir (110-1) and the second reservoir (110-2). The channel (130) has a first heating zone (250-1), a second heating zone (250-2), and a third heating zone (250-3).

A first liquid volume (140-1) and second liquid volume (140-2) obstructs the channel (130) and an immiscible fluid (242) separates the first liquid volume (140-1) and the second liquid volume (140-2). That is, the microfluidic device (200) shows an example using multiple liquid volumes (140). The number of liquid volumes (140) and heating zones (250) may be increased to allow more samples to be processed at a time. In another example, the microfluidic device (200) includes parallel channels (130) between the first and second reservoirs (110).

The immiscible fluid (242) may be a gas. For example, the immiscible fluid (242) may be air, argon, nitrogen, etc. In some examples, the immiscible fluid (242) may be the same as the thermally expandable fluid contained in the reservoirs (110). In other examples, the immiscible fluid (242) is a liquid. The use of a liquid to separate the liquid volumes (140) helps transfer the force against the first liquid volume (140-1) to the second liquid volume (140-2). That is, an immiscible liquid is not as compressible as an immiscible gas. The use of hydrophilic liquid volumes (140) and hydrophobic immiscible fluid (242), e.g., mineral oil, provides one example of an immiscible liquid. Silicones and/or fluorocarbons provide other methods of generating immiscibility.

The heating zones (250) may include heaters in the channel (130). For example, a resistive heater may be placed on the bottom of the channel (130), on a side wall of a channel (130), and/or on an upper surface of the channel (130).

These heaters provides heat to the zone through a wall of the channel (130), for example, by conduction. In an example, an infrared and/or other electromagnetic radiation source is used to selectively heat the heating zones (250). The heating zones (250) may include a modified surface of the channel (130) to preferentially absorb electromagnetic radiation and convert that radiation to heat. In some examples, the heating zones (250) include a temperature sensor. The temperature sensor may measure the temperature of the heating element, the liquid volume (140), and/or the immiscible fluid (242). In an example, the temperature sensor measures the resistivity of a component between two electrodes. For example, the resistance across the resistive element of the resistive heater may be monitored. The temperature sensor may be an indirect sensor, for example, an infrared optical sensor. In an example, a single temperature sensor monitors multiple heating zones (250) simultaneously.

Figure 3:
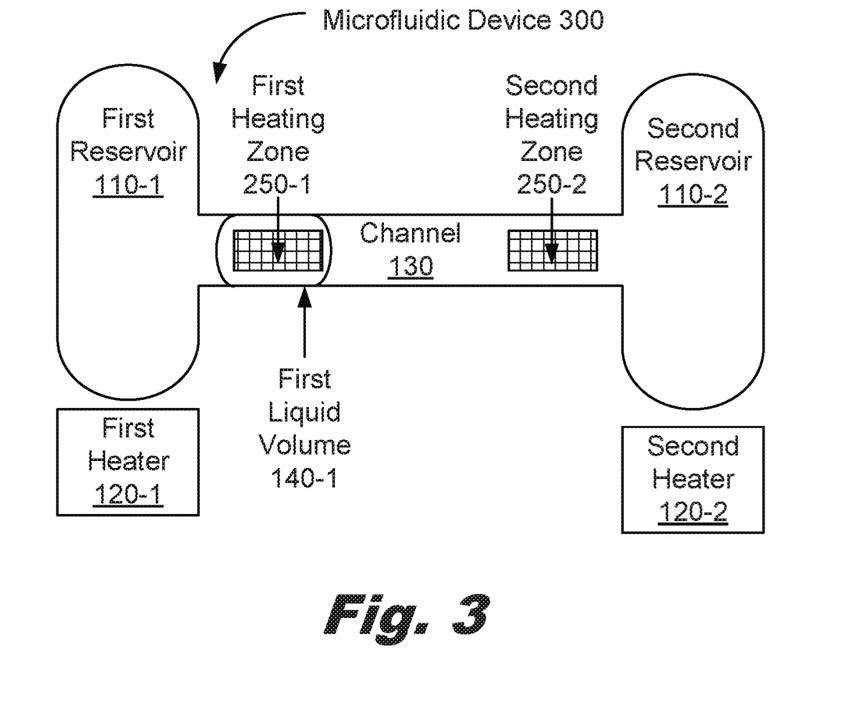
FIG. 3 shows an example of a microfluidic device consistent with this specification.

FIG. 3 shows an example of a microfluidic device (300) consistent with this specification. The microfluidic device (300) includes the first reservoir (110-1), the first heater (120-1), the second reservoir (110-2), a second heater (120-2), the channel (130) with its first heating zone (250-1) and second heating zone (250-2), and the first liquid volume.

Figure 4:
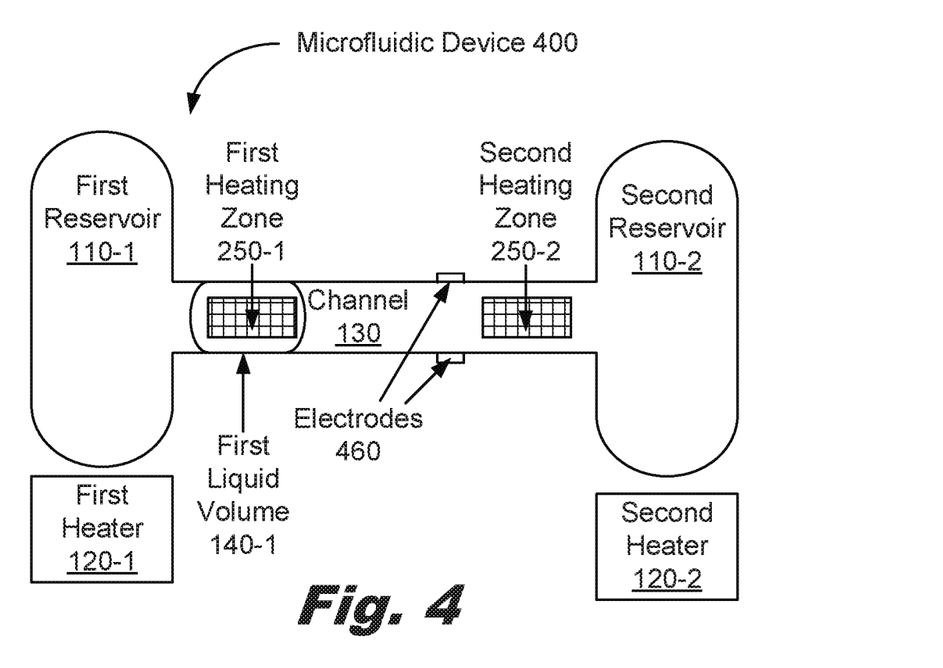
FIG. 4 shows an example of a microfluidic device consistent with this specification.

FIG. 4 shows an example of a microfluidic device (400) consistent with this specification. The microfluidic device (400) includes the first reservoir (110-1), the first heater (120-1), the second reservoir (110-2), the second heater (120-2), the channel (130) with its first heating zone (250-1) and second heating zone (250-2) and the first liquid volume (140-1).

FIG. 4 also depicts an example with a pair of electrodes (460) in the walls of the channel (130). The pair of electrodes (460) may be part of an electrical sensor. For example, the pair of electrodes (460) may enable an electrical measurement. The pair of electrodes (460) may enable measurement of DNA concentration. The electrodes (460) may include functionalized electrodes (460).

Figure 5:
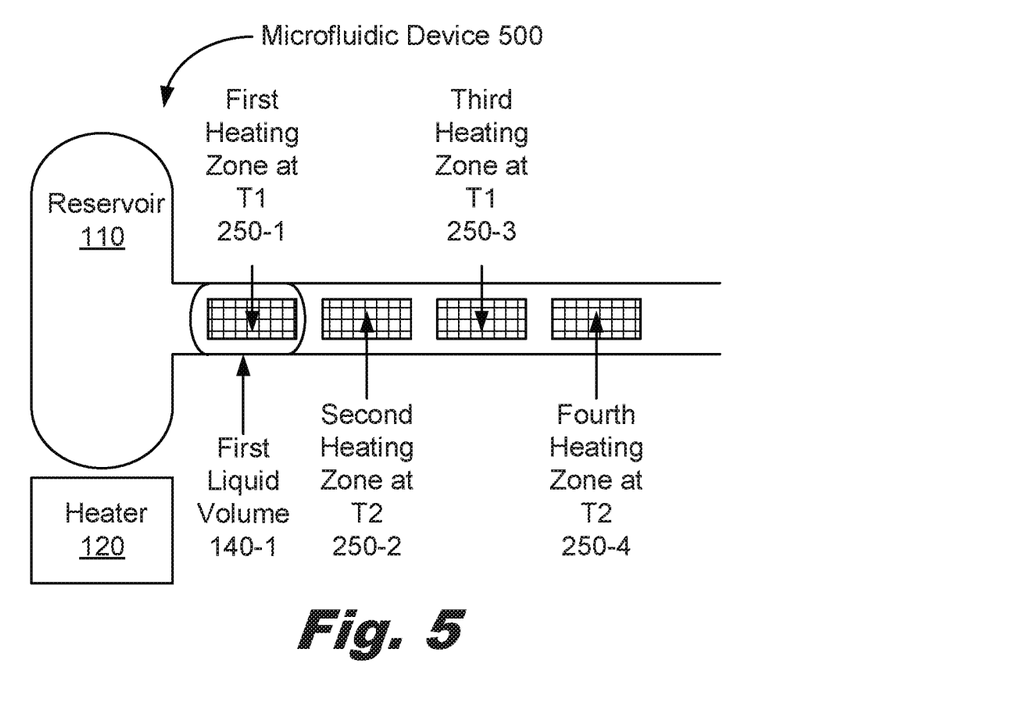
FIG. 5 shows an example of a microfluidic device consistent with this specification.

FIG. 5 shows an example of a microfluidic device (500) consistent with this specification. The microfluidic device (500) depicted in FIG. 5 includes a reservoir (110), a heater (120), and a channel (130) connected to the reservoir (110) and extending from the reservoir (110). In this example, the channel (130) includes a series of heating zones (250), wherein a first set of heating zones including a first heating zone (250-1) and a third heating zone (250-3) are at a first temperature (T1) and a second set of heating zones including a second heating zone (250-2) and a fourth heating zone ((250-4) are at a second temperature (T2) and the heating zones (250) alternate between the first and second set.

The heating zones (250) may support more than two temperatures within the microfluidic device (500). For example, the use of three different temperature heating zones (250) may support annealing, priming, and extension at different temperatures. In other examples, the temperatures of the various operations may be modified during the later (or earlier) cycles. For example, in some cases a higher temperature is used in priming during early cycles to increase successful duplication while a lower priming temperature is used in later cycles to enhance specificity and/or reduce errors. In some examples, the individual heating zones are tunable using a local resistive heater. The heating zones (250) may be all heated to a baseline temperature using a block and/or larger heater with local regions heated even hotter. This may reduce the number of control signals and/or resistive heaters needed for some implementations.

Figure 6:
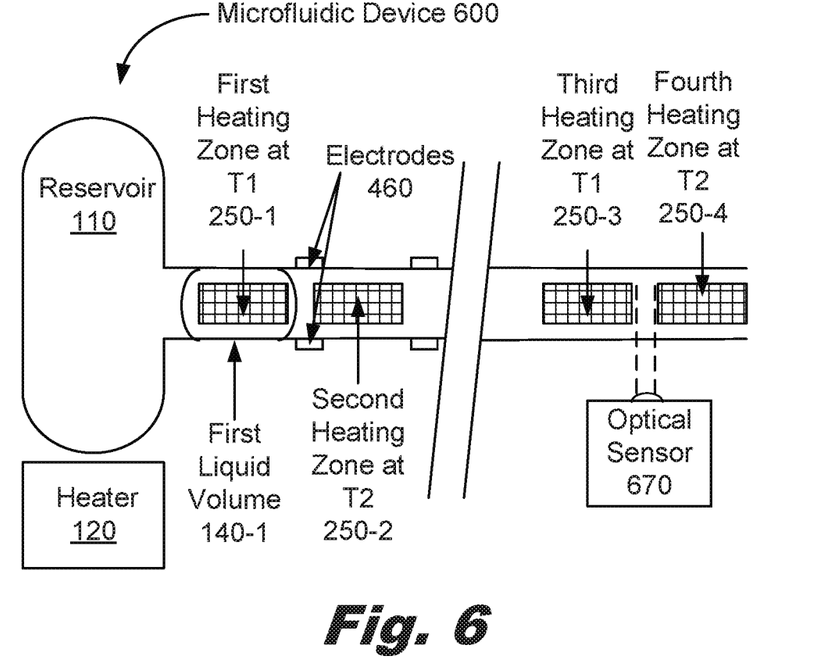
FIG. 6 shows an example of a microfluidic device consistent with this specification.

FIG. 6 shows an example of a microfluidic device (600) consistent with this specification. The microfluidic device (600) of FIG. 6 includes a reservoir (110), a heater (120), and a channel (130) connected to the reservoir (110) and extending from the reservoir (110). In this example, the channel (130) includes a series of heating zones (250), wherein the a first set including a first and third heating zone (250-1, 250-3) is at a first temperature (T1) and a second set including a second and fourth heating zones (250-2, 250-4) are at a second temperature (T2) and the heating zones (250) alternate between the first and second set. The microfluidic device (600) of this example also includes an sensor to image a region between two adjacent heating zones (250). Examples of such sensors include an optical sensor (670) and a pair of electrodes (460) for a conductivity sensor between each pair of adjacent heating zones (250).

The sensor may be used to detect the presence of the liquid volume (140) in a portion of the channel (130). In some examples, the sensor is located between two heating zones (250) and in another example, the sensor may be located in a heating zone (250). In an example, sensors are located along the length of the channel (130). In some examples, the sensor may be used to detect the immiscible fluid (242) between liquid volumes.

In one example, the sensor may be an optical sensor (670). The optical sensor (670) may measure visible wavelengths. In other examples, the optical sensor (670) may measure ultraviolet and/or infrared wavelengths. In an example, the optical sensor (670) provides a temperature estimate of the liquid volume (140) as the liquid volume (140) passes through a portion of the channel (130). In some examples, the optical sensor (670) may detect a probe and/or a nucleic acid concentration.

In some examples, the sensor may be a conductivity sensor. As a specific example, the sensor comprises two electrodes (460) located in the channel (130), e.g., on a wall and/or surface of the channel (130). An electrical property such as impedance, conductance, resistance, current, and/or other electrical property, is measured between the two electrodes (460). In some cases, the sensor detects when an aqueous liquid volume with some conductive ions bridges the two electrodes (460). The sensor may be used to measure a concentration of nucleic material in the liquid volume (140).

As described above, the sensor may detect when the immiscible fluid (FIG. 2, 242) between two liquid volumes (140) bridges the two electrodes (460). For example, one electrode (460) may be located in the channel (130) and a second electrode (460) may be located on a wall of the channel (130) and/or even remote to the channel (130). In other examples, the detection is when one of the electrodes (460) is blocked by a non-conductive fluid. In an example, the non-miscible fluid (242) between two liquid volumes (140) is modified to provide a measureable signal dependent on temperature across the electrodes. For example, an ionic species whose mobility is influenced strongly by temperature may be added to the non-miscible fluid (242). In an example, this may be an ionic liquid for an aqueous liquid volume (140). In an example, this may be a charged organic species, e.g. an anionic and/or cationic surfactant in an oil-based liquid volume (140).

Figure 7:
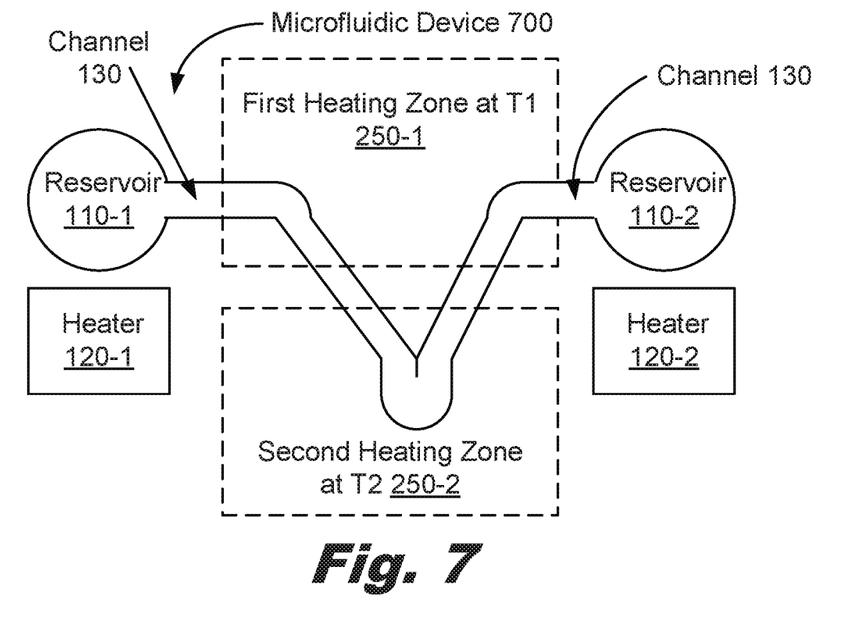
FIG. 7 shows an example of a microfluidic device consistent with this specification.

FIG. 7 shows an example of a microfluidic device (700) consistent with this specification. In this example, the microfluidic device (700) includes two reservoirs (110-1, 110-2), each reservoir (110) having a heater (120-1, 120-2) to heat the fluid in the reservoir and a channel (130) connects the reservoirs (110). The channel (130) passes through multiple heating zones (250). In this example, the channel (130) is not straight. Rather, the channel (130) travels back and forth between the first heating zone (250-1) and the second heating zone (250-2). Doing so allows the use of a single, larger heater for each of the heating zones (250) and may simplify controls compared to trying to control multiple smaller heating zones (250).

The channel (130) may have a sinusoidal and/or wave shape. The channel (130) may have a series of connected arcs. In some examples, the channel (130) width and/or cross-section is varied to be larger at target dwell points. For example, the channel (130) width and/or cross section may be smaller on a distal side of the target dwell points to aid in stopping the liquid volume (140). In one specific example, a heating zone (250) may include an internal secondary heating zone (250). The internal secondary heating zone (250) may use a resistive heater (120) to achieve a higher local temperature, for example, for the melt operation.

Figure 8:
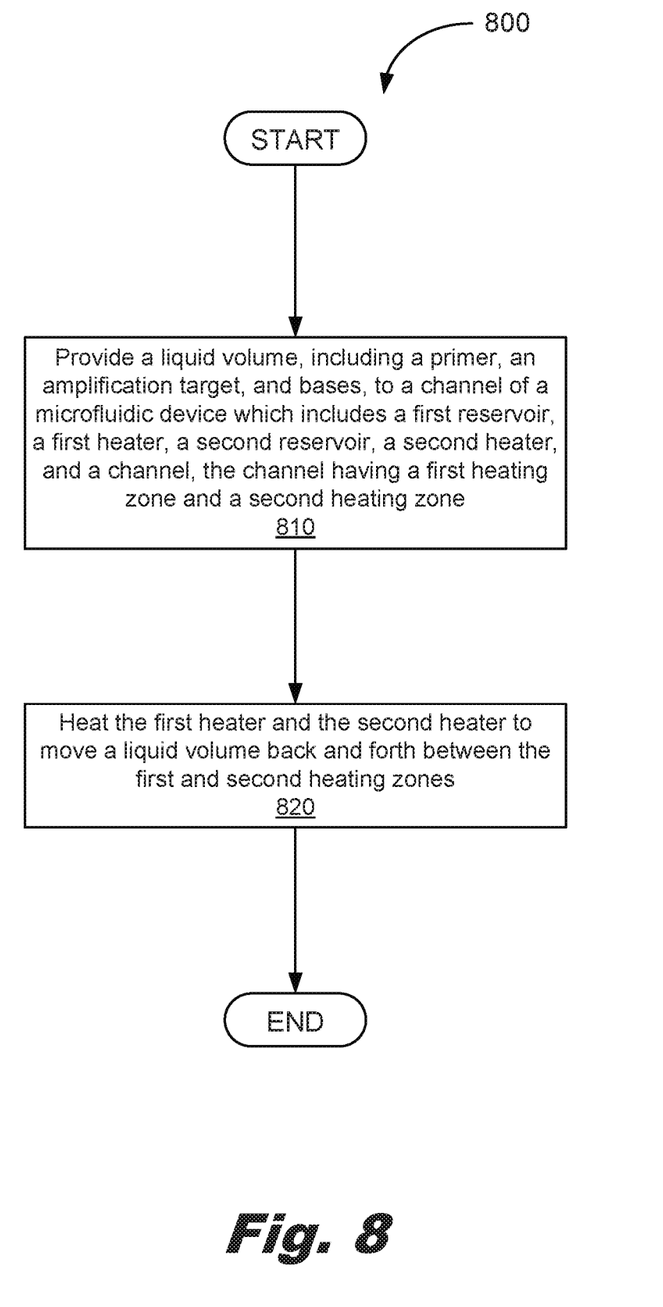
FIG. 8 shows a flowchart of a method of performing Polymerase Chain Reaction (PCR) using a microfluidic device consistent with this specification.

FIG. 8 shows a flowchart of a method (800) of performing Polymerase Chain Reaction (PCR) using a microfluidic device consistent with this specification.

According to the method (800), a liquid volume (140) is provided (810) to a channel (130) of a microfluidic device (300). In this example, the liquid volume (140) includes a primer, an amplification target. As described above, the microfluidic device includes a first reservoir (110-1) containing a thermally expandable fluid and a first heater (120-1) to heat the fluid in the first reservoir (110-1). The microfluidic device also includes a second reservoir (110-2) containing a thermally expandable fluid and a second heater (1200-2) to heat the fluid in the second reservoir (110-2). A channel (130) connects the first reservoir (110-1) and the second reservoir (110-2). The channel (130) includes a first heating zone (250-1) and a second heating zone (250-2). In some examples, the liquid volume (140) may be an oil with aqueous volumes inside the oil, for example to perform digital PCR (dPCR).

According to the method (800), the first heater (250-1) and second heater (250-2) are heated to move the liquid volume (140) back and forth between the first and second heating zones (250) of the channel (130). This is carried out by the expansion of the thermally expandable fluid in the first reservoir (110-1) and second reservoir (110-2) which moves the liquid volume (140).

In some examples, the method (800) may further include detecting the liquid volume (140) between the first heating zone (250-1) and the second heating zone (250-2) using a sensor (670). The sensor (670) may include a pair of electrodes. The sensor (670) may be a resistance sensor. The sensor (670) may be an impedance sensor. The sensor (670) may be a current sensor. The sensor (670) may be an optical sensor (672).

Figure 9A:
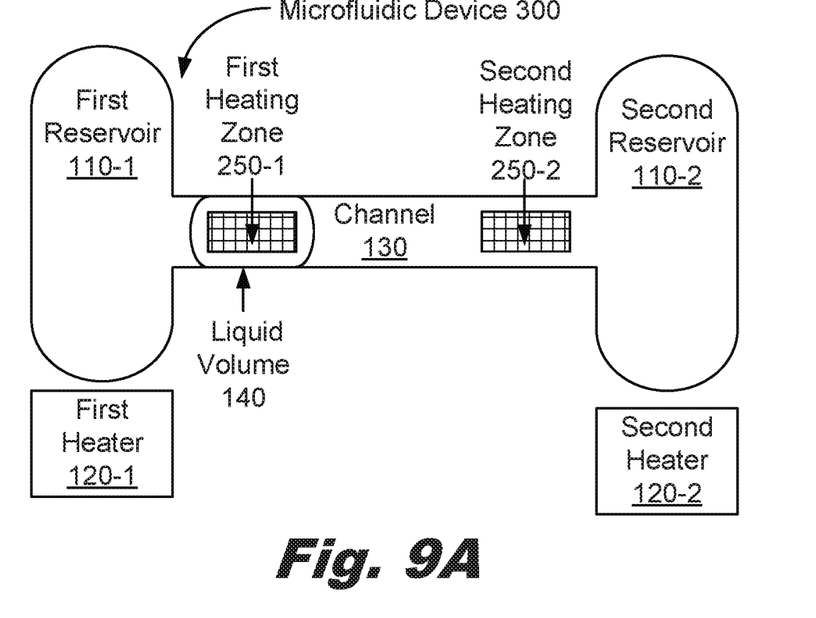
FIGS. 9A and 9B show use of a microfluidic device consistent with this specification to perform PCR.
Figure 9B:
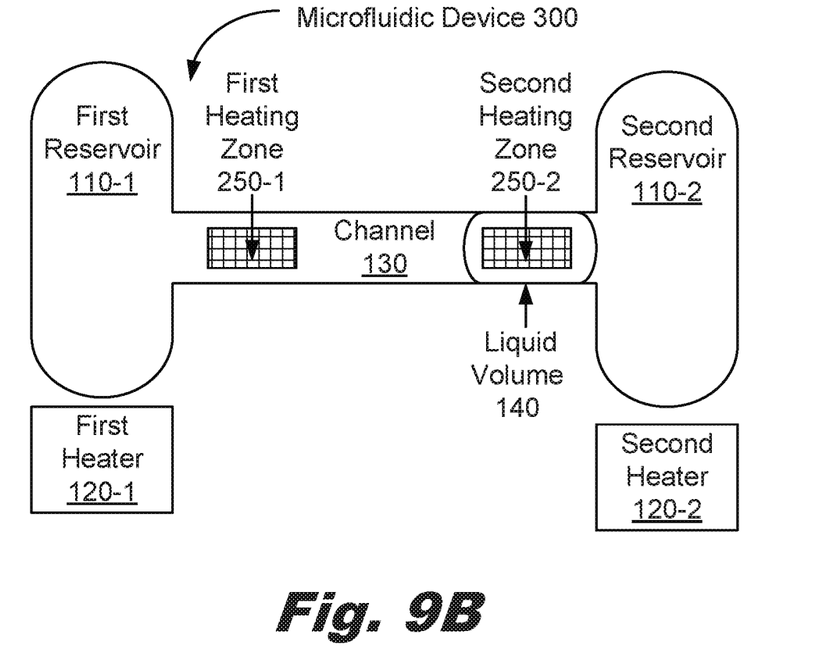

FIGS. 9A and 9B show the use of a microfluidic device (300) consistent with this specification to perform PCR. The microfluidic device (300) of this example includes a first reservoir (110-1) containing a thermally-expandable fluid and a first heater (120-1) to heat the thermally-expandable fluid of the first reservoir (110-1). The microfluidic device (300) also includes a second reservoir (110-2) containing a thermally-expandable fluid and a second heater (120-2) to heat the thermally-expandable fluid of the second reservoir (110-2). A channel (130) connects the first reservoir (110-1) and the second reservoir (110-2). The channel has a first heating zone (250-1) and a second heating zone (250-2). A first liquid volume (140) obstructs the channel (130).

In FIG. 9A, the liquid volume (140) is in the first heating zone (250-1) in the channel (130). The first heating zone (250-1) serves to denature the amplification target in the liquid volume (140). Once the liquid volume (140) has been in the first heating zone (250-1) long enough to denature the amplification target, the first heater (120-1) heats the thermally-expandable fluid in the first reservoir (110-1) which pushes the liquid volume (140) to the second heating zone (250-2) as depicted in FIG. 9B.

In FIG. 9B, the fluid volume (140) is in the second heating zone (250-2) in the channel (30). The second heating zone (250-2) is cooler than the first heating zone (250-1). The second heating zone (250-2) allows the amplification target to be annealed and extended. After the extension cycle is completed, the second heater (120-2) heats the thermally-expandable fluid in the second reservoir (110-2), which causes the fluid to push the liquid volume (140) back to the first heating zone (250-1) as depicted in FIG. 9A. Once in the first heating zone (250-1), the amplification target is denatured and the cycle is repeated.

The channel (130) between the first heating zone (250-1) and the second heating zone (250-2) may include a sensor to detect the presence of the liquid volume (140) or immiscible fluid (242). The heating zones (250) may include temperature sensors to monitor the temperature in the heating zones (250). The temperature sensors may be in the channel (130) or the substrate.

When performing PCR, the liquid volume (140) contains an amplification target, and other components, such as bases. In some examples, the liquid volume (140) contains master mix to provide bases, buffers, etc. for the PCR.

The time the liquid volume (140) spends in each heating zone (250) will depend on a variety of factors, including the particular amplification target, the primers, and the length of the amplification target. However, because the described microfluidic device (300) is heating the liquid volume (140) and not a container (such as a cuvette and/or vial) the described microfluidic device (300) may be able to use shorter cycle times compared to those often used in PCR cyclers. In some examples, the liquid volume (140) includes additional primers (for example, 10× the usual concentration) to increase the speed of the priming operation and reduce the cycle time further.

The denaturation operation may be performed at 92 to 100 degrees C., and preferably at 94 to 98 degrees C. Denaturation may take approximately 20 to 30 seconds. In some examples, shorter times are used, for example in a range of 1 to 5 seconds. The described microfluidic devices (300) with their low thermal mass allow potentially even shorter denaturation phases, for example, on the order of 1-10 milliseconds. Because the exposure time at the higher denaturation temperature may be kept short, higher temperatures may be used without the associated thermal degradation and other issues.

The annealing operation may be performed at 48 to 72 degrees C. Annealing may be primer dependent. Accordingly, having the ability to adjust the annealing temperature independent of the other zones of the microfluidic system allows flexibility to accommodate different primers. Annealing may take approximately 30 seconds. Annealing times may be reduced, for example to between 1 to 10 seconds. Under some conditions, Annealing times may be further reduced to 50 to 500 milliseconds. Because of the low thermal mass of the test sample, the temperature may be rapidly cycled compared with conventional techniques. This may greatly increase the speed and throughput compared with previous PCR temperature-time profiles. Moving to higher throughput speeds is facilitated by higher primer concentrations and higher enzyme (e.g., polymerase) concentrations. For example, the primer concentration may be 10 to 50 times higher than usual PCR concentrations. Similarly, enzyme concentrations may be 10 to 50 times higher than usual PCR concentrations. Higher concentrations of enzymes and primers facilitate shorter cycle times by reducing diffusion times.

Extension may be performed at 68 to 80 degrees C. The extension temperature may vary depending on the particular polymerase used. Depending on the annealing temperature, the extension temperature may overlap with the annealing temperature. Extension time depends on the number of bases to be copied, with 1000 bases a minute being a widely used rule of thumb. This allows rapid cycling of smaller lengths of nucleic material.

In some examples, the FOR cycle is 10 seconds, 2 seconds, 1 second, 0.5, seconds, 0.1 seconds, and/or shorter times. The devices (300) described herein support rapid thermal cycling by moving the liquid volume (140) between heating zones (250) without moving containment or other materials. The liquid volume (140) has a small thermal load being moved through stable thermal zones, allowing rapid heating and/or cooling. Adjustments to the solution composition may facilitate faster cycling.

Figure 10:
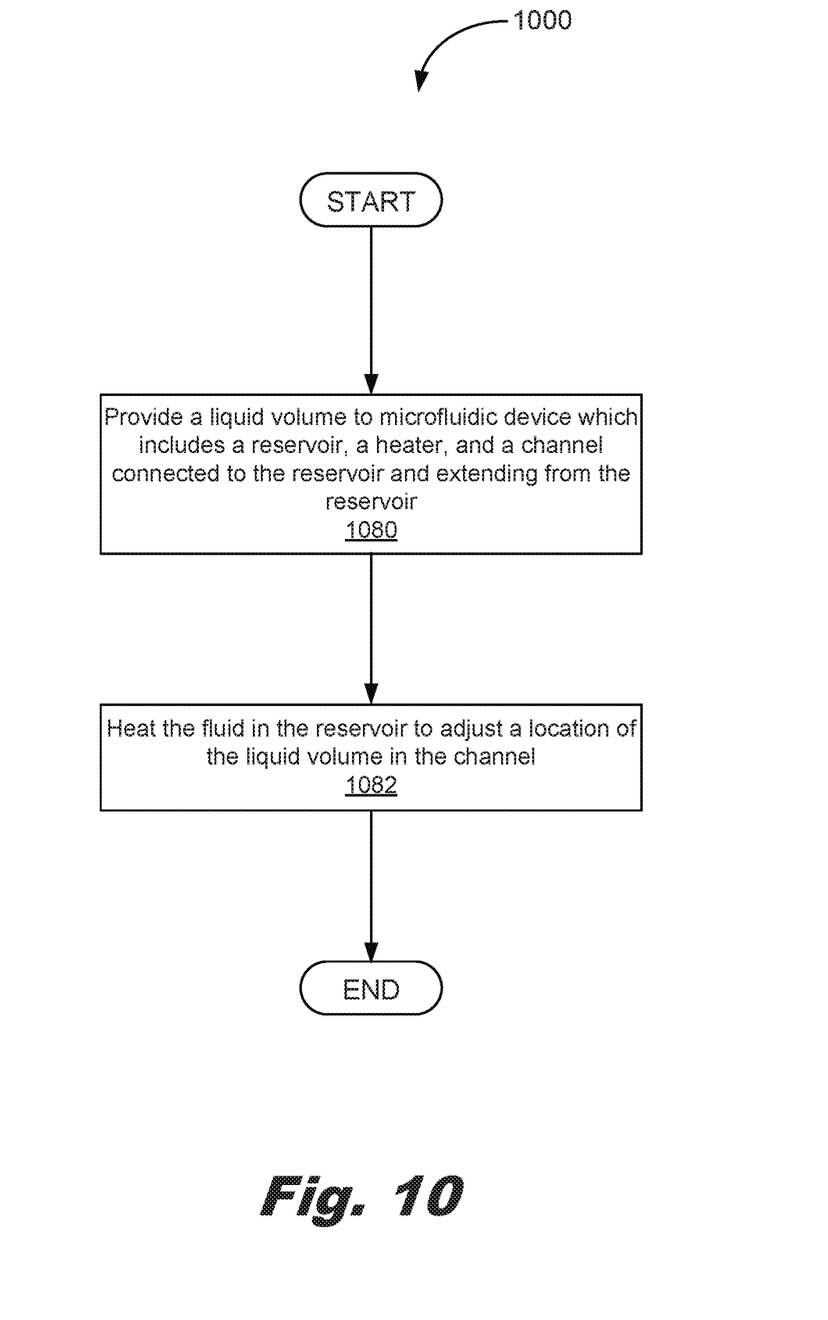
FIG. 10 shows a flowchart for a method of using a microfluidic device consistent with this specification.

FIG. 10 shows a flowchart for a method (1000) of using a microfluidic device (100) consistent with this specification. The method (1000) includes providing (1080) a liquid volume (140) to the microfluidic device (100) and heating (1082) the thermally expandable fluid in the reservoir (110) to adjust a location of the liquid volume (140) in the channel (130), where the heated thermally expandable fluid expands and pushes the liquid volume (140) in the channel (130).

The described microfluidic device (100) includes the reservoir (110), heater (120), and channel (130). The heater (120) acts as an actuator to move the liquid volume (140) in the channel (130). The liquid volume (140) obstructs the channel (130). By using a thermally-expandable fluid such as air, the liquid volume (140) may be isolated from other liquids, keeping the materials in the liquid volume (140) contained. The described microfluidic device (100) may be used to control the position of the liquid volume (140) in the channel (130). With this control, a wide variety of tests and processes may be performed using other components of the microfluidic device (100).

One example of a process that may be performed with such a microfluidic device (100) is PCR. In this example, the reservoir (110) and heater (120) may be used to cycle the liquid volume (140) between a first heating zone (250-1) and a second heating zone (250-2) in the channel (130).

As noted above, the method (100) includes heating (1082) the thermally expandable fluid in the reservoir (110) to adjust a location of the liquid volume (140) in the channel (130). In this example, the heated thermally expandable fluid expands and pushes the liquid volume (140) in the channel (130). In some examples, the heater (120) includes a temperature sensor that is located in the reservoir (110), in the channel (130), or in a substrate near the heater (120). The heater (120) may be a resistive heater or a bank of resistive heaters. In the case of the heater (120) being a bank of resistive heaters, the bank may be distributed non-uniformly on a surface of the reservoir (110) to induce convection of the thermally expandable fluid in the reservoir (110). For example, the bank of resistive heaters may be located near the center of the reservoir (110) to induce circulation of the thermally expandable fluid in the reservoir (110). In an example, a heating zone in the channel (130) may be used to supplement the heating of the heater (120).

The microfluidic device (100) may move the liquid volume (140) between a heating zone (250) and a measurement location in the channel (130). Such a setup may be used to monitor a reaction in the liquid volume (140). After the measurement is made, the microfluidic device (100) may return the liquid volume (140) to the heating zone (250).

The method (1000) may include detecting the adjustment of the liquid volume (140) in the channel (130) using a sensor. In some examples, the sensor makes a measurement of a property of the liquid volume (140). For example, the sensor may measure absorption and/or emission of light from the liquid volume (140). Such measurements may be used to estimate the relative and/or absolute amount of types of chemical bonds in the liquid volume (140).

Nucleic acids show a strong absorbance in the region of 240 to 275 nm. In DNA, the bases are stacked in the hydrophobic core of the double helix. As a result, the absorbance from the bases is decreased relative to the absorbance of single-stranded DNA. Single stranded DNA absorbs less than to oligonucleotides. This property allows monitoring of the progress of a DNA and/or RNA polymerization reaction, for example. This property may also be used to detect melting of an amplification target prior to annealing and extension.

Other techniques to measure precursor and/or product concentrations may be used depending on the specific reactions being performed. For example, impedance measurements may be used to estimate DNA concentration in a solution. In some examples, adding an indicator and/or marker may provide and/or enhance a signal for the sensor. In an example, the sensor is a diode array spectrometer. The described microfluidic device (100) may be used to automate a variety of processes while limiting the potential for contamination.

Hydraulic approaches for moving liquid volumes (140) may allow diffusion into and/or out of the adjacent liquid. In contrast, the microfluidic devices described herein (100) may use a gas as the thermally expandable fluid. This allows the surface tension of the liquid volume (140) to contain the materials of the reaction volume. Because the microfluidic device (100) may have a controlled and contained volume, it may be easier to prevent evaporation of the liquid volume, for example, by using an expandable fluid with high humidity. In an example, the reservoir (110) includes water to provide humidity in the thermally expandable fluid when the fluid is heated. It will be appreciated that, within the principles described by this specification, a vast number of variations exist. It should also be appreciated that the examples described are only examples, and are not intended to limit the scope, applicability, or construction of the claims in any way.

What is claimed is:

1. A microfluidic device comprising:
a first reservoir comprising a thermally expandable fluid;
a second reservoir comprising more thermally expandable fluid;
a heater to selectively heat the thermally expandable fluid in either of the reservoirs;
a channel extending between the two reservoirs; and
a liquid volume to obstruct the channel;
wherein the heater is controllable to oscillate the liquid volume within the channel by alternately heating the thermally expandable fluid in the first and second reservoirs; and
wherein the channel further comprises a first heating zone at a first temperature, and a second heating zone at a second temperature, the first heating zone and the second heating zone being separated by an unheated portion of the channel.

2. The device of claim 1, wherein the thermally expandable fluid is a gas.

3. The device of claim 1, wherein the liquid volume comprises a primer.

4. The device of claim 1, wherein the heater is controllable such that alternating heating of the first reservoir and second reservoir moves the liquid volume between the first heating zone and the second heating zone based on expansion of the thermally expandable fluid in the reservoirs.

5. The device of claim 4, wherein the channel further comprises a third heating zone and the device comprises an additional liquid volume in the channel separated from the liquid volume.

6. The device of claim 5, further comprising an immiscible fluid between the first liquid volume and the second liquid volume.

7. The device of claim 1, further comprising an optical sensor to image a region between two adjacent heating zones.

8. A method comprising:
providing a liquid volume to a microfluidic device, wherein the microfluidic device comprises:
a first reservoir and a second reservoir containing a first thermally expandable fluid and a second thermally expandable fluid, respectively,
one or more heaters to selectively heat the first thermally expandable fluid and the second thermally expandable fluid alternately in the two reservoirs, and
a channel connected and extending between the two reservoirs, wherein the one or more heaters are controllable to oscillate the liquid volume within the channel by alternately heating the first and second thermally expandable fluids in the first and second reservoirs, respectively, and wherein the channel further comprises a first heating zone at a first temperature, and a second heating zone at a second temperature, the first heating zone and the second heating zone being separated by an unheated portion of the channel; and
alternately heating the thermally expandable fluid in the two reservoirs to oscillate a location of the liquid volume in the channel, where a heated thermally expandable fluid expands and pushes the liquid volume in the channel.

9. The method of claim 8, wherein the location of the liquid volume is adjusted between the first heating zone and the second heating zone in the channel.

10. The method of claim 8, further comprising detecting an adjustment of the liquid volume in the channel using a sensor.

11. The method of claim 8, comprising performing a polymerase chain reaction (PCR), wherein:
the liquid volume comprises a primer, an amplification target, and bases, and the one or more heaters of the microfluidic device include a first heater to heat the first thermally expandable fluid in the first reservoir and a second heater to heat the second thermally expandable fluid in the second reservoir; and
heating the first heater and second heater moves the liquid volume back and forth between the first and second heating zones of the channel by expansion of the first thermally expandable fluid and the second thermally expandable fluid in the first reservoir and second reservoir, respectively.

12. The method of claim 11, further comprising detecting the liquid volume between the first heating zone and the second heating zone using a sensor.

13. The method of claim 12, wherein the sensor comprises a pair of electrodes.

14. A microfluidic device comprising:
a first reservoir comprising a thermally expandable fluid;
a second reservoir comprising more thermally expandable fluid;
a heater to selectively heat the thermally expandable fluid in either of the reservoirs;
a channel extending between the two reservoirs, wherein the channel comprises multiple heating zones; and
a liquid volume to obstruct the channel;
wherein the heater is controllable to oscillate the liquid volume within the channel by alternately heating the thermally expandable fluid in the first and second reservoirs; and
wherein the heater alternately heats the thermally expandable fluid in the first and second reservoirs to push the liquid volume back and forth between the multiple heated zones to produce a target time-temperature profile.

15. A microfluidic device comprising:
a first reservoir comprising a thermally expandable fluid;
a second reservoir comprising more thermally expandable fluid;
a heater to selectively heat the thermally expandable fluid in either of the reservoirs;
a channel extending between the two reservoirs;
a first liquid volume and a second liquid volume to obstruct the channel; and
an immiscible fluid to separate the first liquid volume and the second liquid volume.

16. The device of claim 15, wherein the immiscible fluid comprises an immiscible gas.

17. The device of claim 15, wherein the immiscible fluid comprises an immiscible liquid that allows pressure from the thermally expandable fluid on the first liquid volume to be transferred to the second liquid volume.

* * * * *